US00PP36239P2

(12) United States Plant Patent
Carr

(10) Patent No.: US PP36,239 P2
(45) Date of Patent: Nov. 5, 2024

(54) ***ERYSIMUM* PLANT NAMED 'Cdcery1'**

(50) Latin Name: ***Erysimum* hybrid**
Varietal Denomination: Cdcery1

(71) Applicant: Charles Carr, Winchester (GB)

(72) Inventor: Charles Carr, Winchester (GB)

( * ) Notice: Subject to any disclaimer, the term of this patent is extended or adjusted under 35 U.S.C. 154(b) by 0 days.

(21) Appl. No.: 18/603,176

(22) Filed: Mar. 12, 2024

(30) Foreign Application Priority Data

May 15, 2023 (QZ) ..... PBR 20231060

(51) Int. Cl.
*A01H 5/02* (2018.01)
*A01H 6/20* (2018.01)

(52) U.S. Cl.
USPC ..... Plt./263.1
CPC ..... *A01H 6/20* (2018.05)

(58) Field of Classification Search
USPC ..... Plt./263.1
CPC ..... A01H 6/20; A01H 5/02
See application file for complete search history.

*Primary Examiner* — Keith O. Robinson
(74) *Attorney, Agent, or Firm* — Penny J. Aguirre

(57) ABSTRACT

A new cultivar of *Erysimum* plant named 'Cdcery1' that is characterized by its foliage that is silverly dark green in color, its flowers that are vivid red in color with minimal fading, its flowers and leaves that are large in size, its strong and upright stems, its low maintenance, compact plant habit, and its drought resistance.

3 Drawing Sheets

Botanical classification: *Erysimum* hybrid.
Variety denomination: 'Cdcery1'.

BACKGROUND OF THE INVENTION

The present invention relates to a new and distinct cultivar of *Erysimum* of hybrid origin that is botanically known as *Erysimum* 'Cdcery1' and will be referred to hereafter by its cultivar name, 'Cdcery1'. 'Cdcery1' is a new cultivar of wallflower grown for use as an ornamental landscape plant.

The new cultivar derived from a controlled breeding program by the Inventor in Winchester, United Kingdom. The goals of the breeding program are to create new cultivars of *Erysimum* that perform well in the garden and have large flowers in unique colors, compact plant habits, and dark green foliage.

The Inventor made crosses between 2011 and 2016 between unnamed and unpatented plants of *Erysimum* in the Inventor's breeding program as both the female and male parents. The seeds were pooled from the crosses and therefore the exact parents are unknown. 'Cdcery1' was selected as a single unique plant in 2018 from the resulting seedlings of the above crosses.

Asexual propagation of the new cultivar was first accomplished by stem cuttings in Winchester, United Kingdom in 2021 by the Inventor. Asexual propagation by stem cuttings and tissue culture using meristematic tissue has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'Cdcery1' as a unique cultivar of *Erysimum*.

1. 'Cdcery1' exhibits foliage that is silverly dark green in color.
2. 'Cdcery1' exhibits earlier flowering; blooming from spring to summer.
3. 'Cdcery1' exhibits flowers that are vivid red in color with minimal fading.
4. 'Cdcery1' exhibits flowers and leaves that are large in size.
5. 'Cdcery1' exhibits strong and upright stems.
6. 'Cdcery1' exhibits a low maintenance, compact plant habit.
7. 'Cdcery1' exhibits drought resistance.

'Cdcery1' can be most closely compared to the *Erysimum* cultivars 'Red Jep' (U.S. not patented) and 'Bowles Me Away' (U.S. Plant Pat. No. 29,380). 'Red Jep' is similar to 'Cdcery1' in having red color flowers. 'Red Jep' differs from 'Cdcery1' in having a less vigorous growth habit and flowers that are duller red and slightly pink in color and fade more as they mature. 'Bowles Me Away' is similar to 'Cdcery1' in having strong upright stems. 'Bowles Me Away' differs from 'Cdcery1' in having flowers that are purple in color.

STATEMENT REGARDING PRIOR DISCLOSURES BY THE INVENTOR

The Applicant asserts that no publications or advertisements relating to sales, offers for sale, or public distribution occurred more than one year prior to the effective filing date of this application. Any information about the claimed plant would have been obtained from a direct or indirect disclosure from the Inventor. The Applicant claims a prior art exemption under 35 U.S.C. 102(b)(1) for disclosure and/or sales prior to the filing date but less than one year prior to the effective filing date. Disclosures include but may not be limited to website listings by Plantipp, Gardenforum, R.H.S., Gardens illustrated, HortWeek, FloralDaily, shootgardening, gardenia, MandyCanUDigIt, Plantago, Gov. UK, Boom In Business, sohu, Dega Gartenbau, Bloemen, and calameo Futurum 2024.

BRIEF DESCRIPTION OF THE DRAWINGS

The accompanying color photographs illustrate the overall appearance and distinct characteristics of the new *Erysimum*.

The photograph in FIG. 1 was taken of a 6-month-old plants of the new cultivar as grown in a greenhouse in a 21-cm container in Heerhugowaard, The Netherlands.

Figure 2:
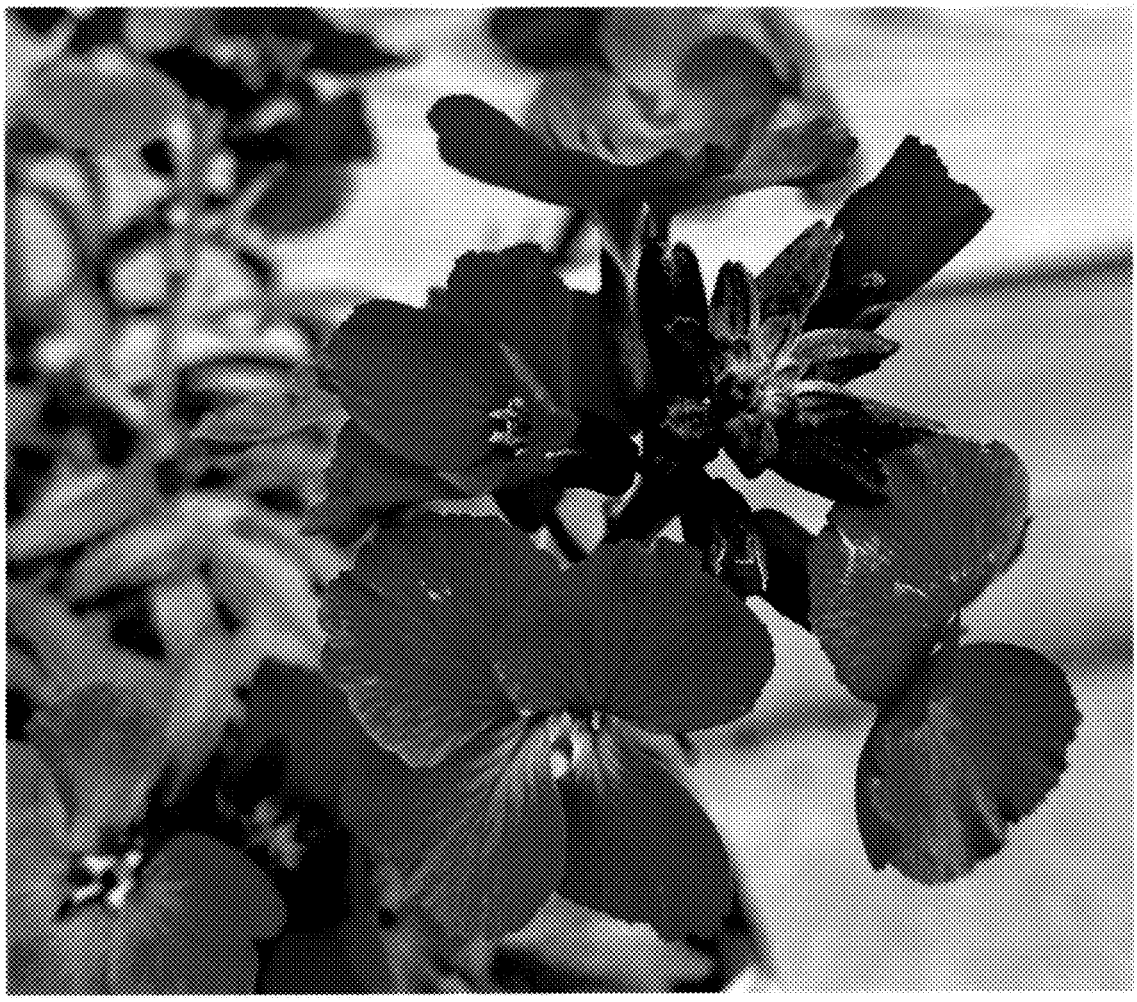
Figure 3:
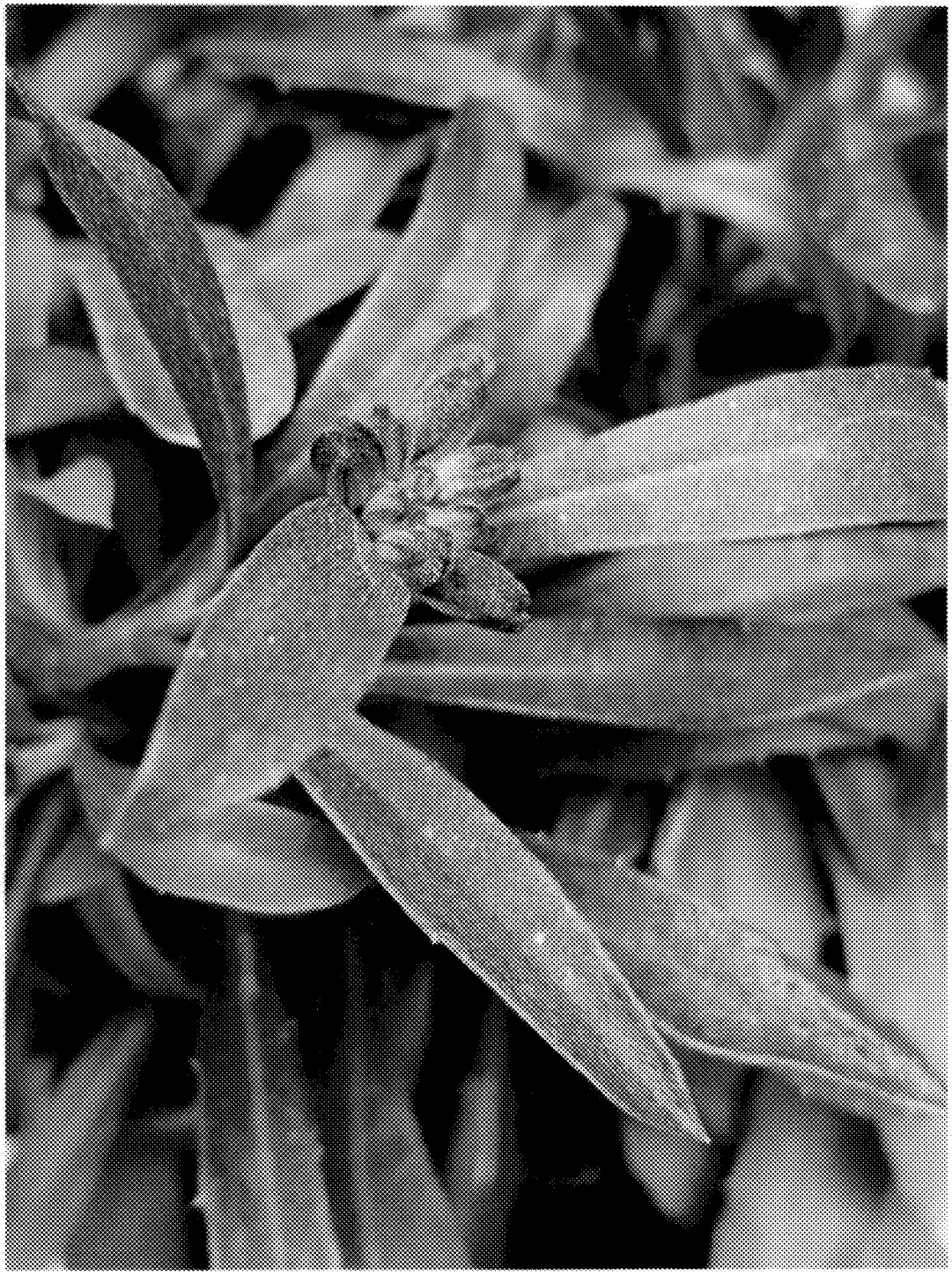

The photographs in FIG. 2 and FIG. 3 were taken of a 6-month-old plant of the new cultivar as grown in a greenhouse in a 21-cm container in Waddinxveen, The Netherlands.

Figure 1:
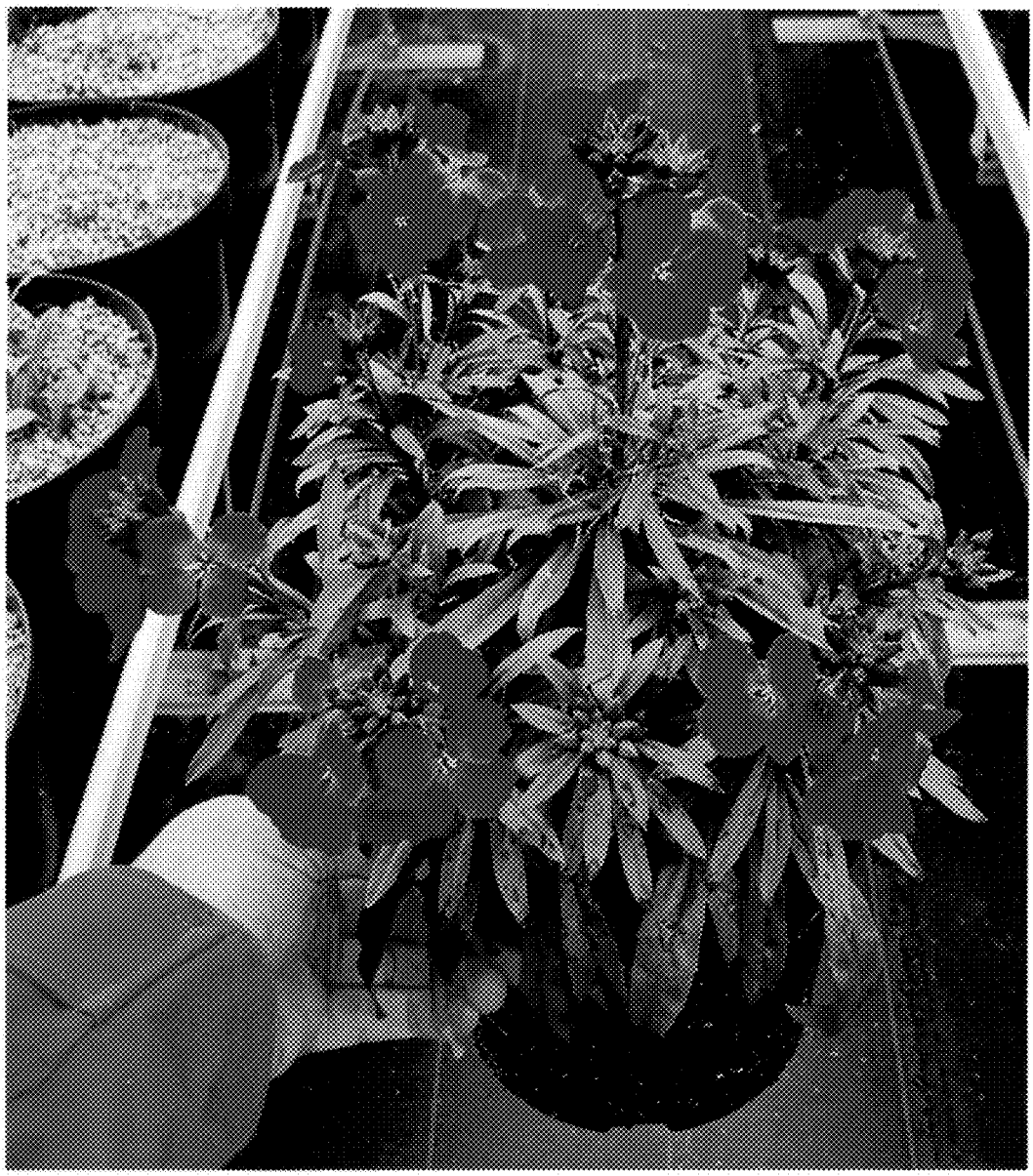

The photograph in FIG. 1 provides a side view of 'Cdcery1' in bloom.

The photograph in FIG. 2 provides a close-up view of an inflorescence of 'Cdcery1'.

The photograph in FIG. 3 provides a close-up view of the foliage of 'Cdcery1'.

The colors in the photographs are as close as possible with the digital photography and printing techniques utilized and the color codes in the detailed botanical description accurately describe the new *Erysimum*.

DETAILED BOTANICAL DESCRIPTION

The following is a detailed description of 6-month-old plants of the new cultivar as grown in a greenhouse in 21-cm containers in Waddinxveen, The Netherlands. The phenotype of the new cultivar may vary with variations in environmental, climatic, and cultural conditions, as it has not been tested under all possible environmental conditions. The color determination is in accordance with The 2015 Colour Chart of The Royal Horticultural Society, London, England, except where general color terms of ordinary dictionary significance are used.

General description:

*Blooming period*.—March to July in The United Kingdom.

*Plant type*.—Herbaceous perennial.

*Plant habit*.—Compact, upright and mounded.

*Height and spread*.—23 cm in height and spread as a 6-month-old plant in a container, reaches 50 cm in height and spread in the landscape.

*Hardiness*.—At least in U.S.D.A. Zone 6 to 9.

*Diseases and pests*.—No susceptibility or resistance to diseases or pests has been observed.

*Root description*.—Fine, fibrous.

*Propagation*.—Stem cuttings and tissue culture.

*Root development*.—6 to 7 weeks for root initiation, 10 to 12 weeks from rooted cutting to young plant in a P17 container.

*Growth habit*.—Moderate.

Stem description:

*Stem size*.—13 cm in length, 7 mm in diameter.

*Stem shape*.—Round.

*Stem color*.—137A to 137B, older wood; 199C.

*Stem surface*.—Slightly pubescent.

*Stem aspect*.—Held nearly upright.

*Internode length*.—An average of 1.2 cm.

*Branching habit*.—Well-branched, 1 main stem, average of 7 lateral branches per main stem.

Foliage description:

*Leaf shape*.—Narrowly oblanceolate.

*Leaf division*.—Simple.

*Leaf base*.—Attenuate.

*Leaf apex*.—Acute.

*Leaf venation*.—Pinnate, both surfaces 144A in color.

*Leaf margins*.—Entire to dentate.

*Leaf attachment*.—Sessile.

*Leaf arrangement*.—Alternate.

*Leaf surface*.—Densely pubescent.

*Leaf color*.—Mature upper surface; 137C margins, mature lower surface; 137D, young upper surface; 137B, young lower surface; 137B.

*Leaf size*.—8.5 cm in length and 1.3 cm in width when mature.

*Leaf quantity*.—An average of 24 per stem.

Flower description:

*Inflorescence type*.—Terminal raceme.

*Inflorescence quantity*.—Average of 10 per plant.

*Lastingness of inflorescence*.—Average of 7 days.

*Inflorescence size*.—An average of 6.2 cm in height and width.

*Flower fragrance*.—Light sweet fragrant.

*Flower number*.—Average of 7 open at one time.

*Flower aspect*.—Upright to outward, dependant on location of the inflorescence.

*Flower bud*.—An average of 1 cm in length and 4 mm in width, ovoid in shape, color; 79A, flushed with N79B.

*Flower type*.—Single.

*Flower size*.—Average of 3.1 cm in depth and diameter.

*Calyx*.—Tubular in form, an average of 1 cm in length and 6 mm in diameter.

*Sepals*.—4, lanceolate in shape, average of 1 cm in length and 2 mm in width, base truncate, entire margins, surfaces are glabrous, color; inner surface 79A, flushed with a hint of 137C, outer surface N79A and 79B.

*Petals*.—4, broadly obovate in shape, obtuse apex, attenuate base, entire margins, an average of 1.5 cm in length and 1.6 cm in width, color; young upper and lower surface N34A, center 34B, mature upper and lower surface 60A, center 70A, veins 71A.

*Peduncles*.—Round in shape, strong, an average of 7.5 cm in length, 3 mm in width, pubescent surface, 137B in color.

*Pedicels*.—Round in shape, strong, an average of 4 mm in length, 1 mm in width, pubescent surface, color; 137C, flushed with N77A.

Reproductive organs:

*Gynoecium*.—Pistil; 1, 8 mm in length, stigmas; 1 mm in length, round in shape, 145B in color, style; 6 mm in length, 145C in color, ovary; not observed.

*Androecium*.—Stamens; 6, anthers; oblong, 3 mm in length, 4D in color, filaments; adnate to corolla, 7 mm in length, 145B in color, pollen; moderate, 4D in color.

*Seeds*.—Not observed.

It is claimed:

1. A new and distinct cultivar of *Erysimum* plant named 'Cdcery1' as herein illustrated and described.

* * * * *